United States Patent [19]

Hofmeister et al.

[11] 4,390,530
[45] Jun. 28, 1983

[54] 3-DEOXY-Δ[15]-STEROIDS

[75] Inventors: Helmut Hofmeister; Rudolf Wiechert; Klaus Annen; Henry Laurent; Sybille Beier, all of Berlin, Fed. Rep. of Germany

[73] Assignee: Schering, A.G., Berlin, Fed. Rep. of Germany

[21] Appl. No.: 233,350

[22] Filed: Feb. 11, 1981

[30] Foreign Application Priority Data

Feb. 11, 1980 [DE] Fed. Rep. of Germany ....... 3005374

[51] Int. Cl.³ .................. A61K 31/56; C07J 11/00; C07J 17/00
[52] U.S. Cl. .................. 424/238; 260/239.5; 260/239.55 R; 260/397.3; 260/397.45; 260/397.5
[58] Field of Search .................. /Steroids MS File; 260/397.5

[56] References Cited

U.S. PATENT DOCUMENTS 3,503,959 3/1970 Christiansen .................. 260/239.5

FOREIGN PATENT DOCUMENTS 34114 8/1981 European Pat. Off. ......... 260/397.5

Primary Examiner—Elbert L. Roberts
Attorney, Agent, or Firm—Millen & White

[57] ABSTRACT

3-Deoxy-Δ[15]-steroids of the formula

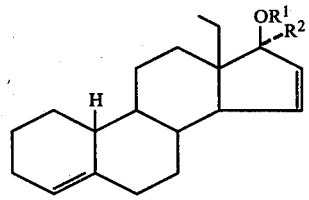

wherein
$R^1$ is hydrogen or an acyl group of a $C_{1-15}$ hydrocarbon carboxylic acid, and
$R^2$ is ethynyl, chloroethynyl or propynyl are valuable progestationally effective compounds having low attendant androgenic side effects.

12 Claims, No Drawings

3-DEOXY-Δ15-STEROIDS

The present invention relates to 3-deoxy-Δ15-steroids, a process for their production, as well as pharmaceutical preparations containing them.

SUMMARY OF THE INVENTION

It is an object of the present invention to provide new steroidal compounds having valuable pharmacological properties.

Upon further study of the specification and appended claims, further objects and advantages of this invention will become apparent to those skilled in the art.

These objects have been attained by providing 3-deoxy-Δ15-steroids of formula I

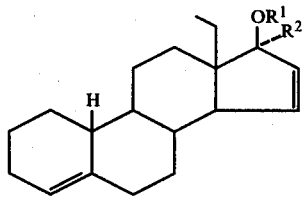

wherein
R$^1$ is hydrogen or acyl and
R$^2$ is ethynyl, chloroethynyl or propynyl.

These novel 3-deoxy-Δ15-steroids are distinguished by a strong progestational activity and a very low androgenic side effect.

DETAILED DISCUSSION

The nature of the acyl group for R$^1$ is not critical and they can be derived from the acids usually employed for esterifications in steroid chemistry. Preferred acids are organic hydrocarbon carboxylic acids of up to 15 carbon atoms, especially lower and intermediate aliphatic carboxylic acids of up to 7 carbon atoms. The acids can also be unsaturated, branched, polybasic, or substituted in the usual way, for example by hydroxy, acyloxy, alkoxy, oxo, amino or halogen. Suitable, furthermore, are cycloaliphatic, aromatic, mixed aromatic-aliphatic, and heterocyclic acids which can likewise be substituted in the usual way. All of these are equivalents, e.g., the heterocyclic acids are equivalent to the hydrocarbon acids.

The following carboxylic acids are examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, β-cyclopentylpropionic acid, cyclohexylacetic acid, cyclohexanecarboxylic acid, phenylacetic acid, phenoxyacetic acid, mono-, di-, and tri-chloroacetic acids, aminoacetic acid, diethylaminoacetic acid, piperidinoacetic acid, morpholinoacetic acid, lactic acid, O-tridecanoylglycolic acid, succinic acid, adipic acid, benzoic acid, nicotinic acid, isonicotinic acid, furan-2-carboxylic acid, etc.

The novel 3-deoxy-Δ15-steroids of formula I can be prepared by introducing the R$^2$ residue into the 17-position of an 18-methyl-4,15-estradien-17-one of formula II,

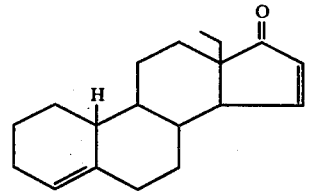

using an agent which yields this residue R$^2$ according to conventional methods, thereby forming a tertiary carbinol, and then, optionally, esterifying the 17-hydroxy group.

The introduction of the R$^2$ residue can be conducted according to conventional methods using an organometallic ethynyl, chloroethynyl or propynyl compound. Such organometallic compounds include, for example, alkali metal acetylides, e.g., potassium and lithium acetylide, potassium and lithium chloroacetylide, or potassium and lithium methylacetylide.

The organometallic compound can also be formed in situ and reacted with the 17-ketone of formula II. Thus, the 17-ketone can be treated, for example, in a suitable solvent with acetylene and an alkali metal, especially potassium, sodium, or lithium in the presence of a C$_4$- or C$_5$-alcohol, or in the presence of ammonia, or in the form, for example, of butyllithium. Lithium chloroacetylide can be formed from 1,2-dichloroethylene and an ethereal methyllithium solution.

Suitable as the organometallic ethynyl compounds are also ethynylmagnesium or ethynylzinc halides, especially ethynylmagnesium bromide or iodide.

Suitable solvents include dialkyl ethers, tetrahydrofuran, dioxane, benzene, toluene, etc. Typical reaction temperatures are −78° to 60° C., and reaction times 0.5 to 2 hours. The reaction is usually conducted under an inert atmosphere such as argon.

The optional subsequent esterification of the 17-hydroxy group can also be conducted according to methods customarily employed in steroid chemistry for the esterification of tertiary hydroxy groups. A suitable esterification method is, for instance, the reaction of the steroids with acid anhydrides or acid chlorides in the presence of alkaline catalysts, e.g., sodium bicarbonate, potassium bicarbonate, potassium carbonate, sodium hydroxide, potassium hydroxide, pyridine, lutidine, collidine, or 4-dimethylaminopyridine. According to a preferred process, the esterification is carried out in the presence of pyridine and 4-dimethylaminopyridine.

The 18-methyl-4,15-estradien-17-one of formula II utilized as the starting material for the process of this invention can be prepared from 3,3-ethylenedithio-15-hydroxy-18-methyl-4-estren-17-one (DOS [German Unexamined Laid-Open Application] 2,749,104) as follows:

At room temperature, 12.9 g of 3,3-ethylenedithio-15α-hydroxy-18-methyl-4-estren-17-one in 250 ml of tetrahydrofuran (THF) is combined with 25 ml of dihydropyran and 0.05 ml of phosphorus oxychloride. After 3 hours, the solution is diluted with ethyl acetate, washed with water, and dried. Chromatography of the crude product on silica gel with 4.5–6% acetone/hexane yields 12.6 g of 3,3-ethylenedithio-18-methyl-15α-tetrahydropyran-2-yloxy-4-estren-17-one, mp 181.9° C.

At 0° C., 1.0 g of 3,3-ethylenedithio-18-methyl-15α-tetrahydropyran-2-yloxy-4-esten-17-one in 20 ml of THF is combined with 2.5 ml of diisobutyl aluminum hydride (20% solution in toluene). After 30 minutes, the solution is diluted with ethyl acetate, washed with water, and dried, thus obtaining 900 mg of 3,3-ethylenedithio-18-methyl-15α-tetrahydropyran-2-yloxy-4-estren-17β-ol as an oil. $[α]_D^{20} = +75°$.

At $-70°$ C., 250 ml of liquid ammonia is combined under agitation with 1.4 g of lithium in small pieces. After 30 minutes, 6.5 g of 3,3-ethylenedithio-18-methyl-15α-tetrahydropyran-2-yloxy-4-estren-17β-ol in 180 ml of THF is added dropwise, the reaction mixture is stirred for 1.5 hours, and then combined with 100 ml of ethanol. After removing ammonia by evaporation, the residue is dissolved in ethyl acetate, washed with water, and dried under vacuum. Chromatography of the crude product (6.0 g) on silica gel with 7.5–10% acetone/hexane yields 2.9 g of 18-methyl-15α-tetrahydropyran-2-yloxy-4-estren-17β-ol as an oil. $[α]_D^{20} = +69.4°$.

At 0° C., 2.6 g of 18-methyl-15α-tetrahydropyran-2-yloxy-4-estren-17β-ol in 50 ml of methylene chloride is stirred with 3.6 g of pyridinium chlorochromate and 1.2 g of sodium acetate at 0° C. After 3.5 hours, the mixture is diluted with methylene chloride, washed with water, and dried. Chromatography of the crude product on silica gel with 3–3.5% acetone/hexane yields 1.6 g of 18-methyl-15α-tetrahydropyran-2-yloxy-4-estren-17-one as an oil. $[α]_D^{20} = +87.4°$.

At room temperature, 28 g of 18-methyl-15α-tetrahydropyran-2-yloxy-4-estren-17-one in 250 ml of ethanol is stirred for 2.5 hours with 30 ml of semiconcentrated hydrochloric acid. The mixture is neutralized with sodium bicarbonate solution and concentrated under vacuum. The residue is dissolved in ethyl acetate, washed with water, and dried. The crude product is chromatographed on silica gel. With 2–2.5% acetone/hexane, 7.1 g of 15α-hydroxy-18-methyl-4-estren-17-one is eluted, mp 70.1° C.

In an ice bath, 7.8 g of 15α-hydroxy-18-methyl-4-estren-17-one in 50 ml of pyridine is combined with 10 ml of methanesulfonic acid chloride. After 1 hour, 50 ml of dimethylformamide (DMF) is added thereto, along with 23 g of anhydrous sodium acetate. The mixture is stirred for another 20 hours at room temperature. The mixture is introduced into ice/water. The thus-precipitated product is vacuum-filtered, washed with water, dissolved in ethyl acetate, and dried. Crystallization from ethyl acetate yields 5.1 g of 18-methyl-4,15-estradien-17-one, mp 125.2° C.

The novel 3-deoxy-Δ15-steroids of this invention are pharmacologically active compounds. They exhibit a spectrum of activity similar to that of steroids oxygenated in the 3-position and are progestationally effective, in particular. For example, in the Clauberg test 17α-ethynyl-18-methyl-4,15-estradien-17β-ol (A) shows a progestational activity comparable to that of the corresponding oxygenated compound. At the same time, it has been found that compound A of this invention has only a minor androgenic activity in the conventional levator aniseminal vesicle test on male castrated rats.

The compounds of this invention can be employed, for example, in contraceptive preparations. In this connection, they can be used as the progestational component in combination with an estrogenically active hormone component, e.g., ethynylestradiol, or as the sole active component. The compounds can also be utilized, however, in preparations for the treatment of gynecological disorders such as cycle irregularities in case of inadequate function of the corpus luteum, climacteric complaints, depressive mood, etc.

For use, the novel compounds can be conventionally processed into the customary medicinal formulations, together with additives, vehicles and flavoring agents conventional in galenic pharmacy, in accordance with conventional methods. They can thus be used for administration to mammals, including humans. Especially suitable for oral administration are tablets, dragees, capsules, pills, suspensions or solutions. Particularly useful for parenteral administration are oily solutions, e.g., sesame oil or castor oil solutions which optionally can also contain a diluent, for example benzyl benzoate or benzyl alcohol.

The concentration or amount of active ingredient is dependent on the form of administration. Thus, for example, tablets for oral administration preferably contain 0.01–0.5 mg of active agent, and solutions for parenteral administration preferably contain 1–100 mg of active compound per 1 ml of solution.

The dosage of the compounds of this invention will conventionally vary with the form and purpose of administration. For example, the daily contraceptive dose upon oral administration is 0.01–0.5 mg administered analogously to the known progestogen norgestrel (U.S. Pat. No. 3,959,322). For treatment of gynecological disorders, typical dosages are 0.05–0.5 mg/day, administered analogously to the known agent cycloprogynova (R).

Dosages for a given host can be determined, e.g., by customary comparison of the activities of the subject compound of a known agent by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

17α-Ethynyl-18-methyl-4,15-estradien-17β-ol

Acetylene is passed for 30 minutes through a solution of 15 ml of butyllithium (15% in hexane) in 50 ml of tetrahydrofuran (THF) (absolute) cooled with ice/water. While conducting argon into the reaction mixture, 500 mg of 18-methyl-4,15-estradien-17-one in 10 ml of THF is then gradually added. After 1 hour, the mixture is combined with saturated ammonium chloride solution, diluted with ether, washed with water, and dried, thus obtaining 450 mg of 17α-ethynyl-18-methyl-4,15-estradien-17β-ol as an oil, mp 83.6° C. (pentane).

EXAMPLE 2

17α-Chloroethynyl-18-methyl-4,15-estradien-17β-ol

Under argon at 0° C., 7 ml of a 5% ethereal methyllithium solution is added dropwise to 1.1 ml of 1,2-dichloroethylene in 10 ml of absolute ether. After 30 minutes, 430 mg of 18-methyl-4,15-estradien-17-one in 15 ml of THF is added; the mixture is stirred for another 15 minutes, combined with saturated ammonium chloride solution, diluted with ether, and the solution washed with water. The crude product is chromatographed on silica gel with acetone/hexane, thus obtaining 310 mg of 17α-chloroethynyl-18-methyl-4,15-estradien-17β-ol as an oil. $[\alpha]_D^{20} = -98°$.

EXAMPLE 3

18-Methyl-17α-propyn-1-yl-4,15-estradien-17β-ol

Methylacetylene is conducted for about 30 minutes through a solution of 20 ml of n-butyllithium (15% in hexane) in 80 ml of absolute THF, cooled with ice/water. Under argon, 800 mg of 18-methyl-4,15-estradien-17-one in 20 ml of THF is then added dropwise, and the reaction mixture is stirred at room temperature. After 20 minutes, the mixture is combined with saturated ammonium chloride solution, diluted with ether, and washed with water. The crude product is chromatographed on silica gel with acetone/hexane, thus obtaining 540 mg of 18-methyl-17α-propyn-1-yl-4,15-estradien-17β-ol as an oil.

EXAMPLE 4

17β-Acetoxy-17α-ethynyl-18-methyl-4,15-estradiene

At room temperature, 1.0 g of 17α-ethynyl-18-methyl-4,15-estradien-17β-ol in 10 ml of pyridine is reacted with 7 ml of acetic anhydride while adding 100 mg of 4-dimethylaminopyridine. The mixture is introduced into ice/water after 4 hours. The thus-precipitated product is vacuum-filtered, dissolved in ethyl acetate, and washed with water. After chromatography of the crude product on silica gel with acetone/hexane, 670 mg of 17β-acetoxy-17α-ethynyl-18-methyl-4,15-estradiene is obtained as a foamy product.

EXAMPLE 5

17β-Butyryloxy-17α-ethynyl-18-methyl-4,15-estradiene 230 mg of 17α-ethynyl-18-methyl-4,15-estradien-17β-ol in 3 ml of pyridine is stirred at room temperature with 1.5 ml of butyric anhydride and 60 mg of 4-dimethylaminopyridine. After 5 hours, the mixture is introduced into ice/water, extracted with ethyl acetate, and washed with water. The crude product is chromatographed on silica gel with ethyl acetate/hexane, thus obtaining 160 mg of 17β-butyryloxy-17α-ethynyl-18-methyl-4,15-estradiene as an oil.

EXAMPLE 6

17α-Ethynyl-17β-heptanoyloxy-18-methyl-4,15-estradiene 300 mg of 17α-ethynyl-18-methyl-4,15-estradien-17β-ol in 4 ml of pyridine is stirred at room temperature with 2 ml of enanthic anhydride and 60 mg of 4-dimethylaminopyridine for 18 hours. The mixture is poured into ice/water, extracted with ethyl acetate, and the solution washed with water. After chromatography of the crude product on silica gel with ethyl acetate/hexane, 190 mg of 17α-ethynyl-17β-heptanoyloxy-18-methyl-4,15-estradiene is obtained as an oil.

EXAMPLE 7

17β-Acetoxy-17α-chloroethynyl-18-methyl-4,15-estradiene

As described in Example 4, 570 mg of 17α-chloroethynyl-18-methyl-4,15-estradien-17β-ol in 6 ml of pyridine is reacted with 3 ml of acetic anhydride and 50 mg of 4-dimethylaminopyridine. After the reaction mixture has been worked up and chromatographed with ethyl acetate/hexane, 390 mg of 17β-acetoxy-17α-chloroethynyl-18-methyl-4,15-estradiene is obtained as a foamy product.

EXAMPLE 8

17β-Butyryloxy-18-methyl-17α-propyn-1-yl-4,15-estradiene

At room temperature, 140 mg of 18-methyl-17α-propyn-1-yl-4,15-estradien-17β-ol in 2.5 ml of pyridine is agitated with 1 ml of butyric anhydride and 60 mg of 4-dimethylaminopyridine. After 8 hours, the solution is introduced into ice/water, extracted with ethyl acetate, washed with water, and the crude product is chromatographed on silica gel with ethyl acetate/hexane, thus obtaining 65 mg of 17β-butyryloxy-18-methyl-17α-propyn-1-yl-4,15-estradiene as an oil.

EXAMPLE 9

(Composition of a Tablet)

| | |
|---|---|
| 0.075 mg | 17α-Ethynyl-18-methyl-4,15-estradien-17β-ol |
| 0.030 mg | 17α-Ethynylestradiol |
| 109.895 mg | Lactose (DAB 6) |
| 8.000 mg | Corn starch (USP XVI) |
| 1.000 mg | Magnesium stearate (USP XVI) |
| 1.000 mg | Talc |
| 120.000 mg | Total weight of tablet |

EXAMPLE 10

(Composition of a Dragee)

| | |
|---|---|
| 0.100 mg | 17α-Ethynyl-18-methyl-4,15-estradien-17β-ol |
| 0.020 mg | 17α-Ethynylestradiol |
| 31.880 mg | Lactose |
| 18.425 mg | Corn starch |
| 2.060 mg | Polyvinylpyrrolidone 25 |
| 0.010 mg | Methylparaben |
| 0.005 mg | Propylparaben |
| 2.500 mg | Talc |
| 55.000 mg | Total weight of tablet, which latter is made into a dragee of about 90 mg with the usual sugar mixture. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3-deoxy-Δ$^{15}$-steroid of the formula

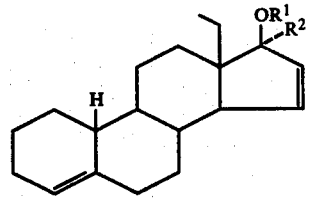

wherein
R$^1$ is hydrogen or an acyl group of a C$_{1-15}$ hydrocarbon carboxylic acid, and $R^2$ is ethynyl, chloroethynyl or propynyl.

2. 17α-Ethynyl-18-methyl-4,15-estradien-17β-ol, a compound of claim 1.

3. 17α-Chloroethynyl-18-methyl-4,15-estradien-17β-ol, a compound of claim 1.

4. 18-Methyl-17α-propyn-1-yl-4,15-estradien-17β-ol, a compound of claim 1.

5. 17β-Acetoxy-17α-ethynyl-18-methyl-4,15-estradiene, a compound of claim 1.

6. 17β-Butyryloxy-17α-ethynyl-18-methyl-4,15-estradiene, a compound of claim 1.

7. 17α-Ethynyl-17β-heptanoyloxy-18-methyl-4,15-estradiene, a compound of claim 1.

8. 17β-Acetoxy-17α-chloroethynyl-18-methyl-4,15-estradiene, a compound of claim 1.

9. 17β-Butyryloxy-18-methyl-17α-propyn-1-yl-4,15-estradiene, a compound of claim 1.

10. A compound of claim 1 wherein $R^1$ is $C_{1-7}$ alkanoyl.

11. A pharmaceutical composition comprising a progestationally effective amount of a compound of claim 1 and a pharmaceutically acceptable carrier.

12. A method of achieving contraceptive effects in a patient in need of the same comprising administering a progestationally effective amount of a compound of claim 1.

* * * * *